United States Patent [19]
Tapolsky et al.

[11] Patent Number: 6,159,498
[45] Date of Patent: Dec. 12, 2000

[54] BIOERODABLE FILM FOR DELIVERY OF PHARMACEUTICAL COMPOUNDS OF MUCOSAL SURFACES

[75] Inventors: Gilles H. Tapolsky; David W. Osborne, both of The Woodlands, Tex.

[73] Assignee: Virotex Corporation, The Woodlands, Tex.

[21] Appl. No.: 09/144,827

[22] Filed: Sep. 1, 1998

Related U.S. Application Data

[63] Continuation of application No. 08/734,519, Oct. 18, 1996, Pat. No. 5,800,832.

[51] Int. Cl.⁷ .......................... A61K 9/70; A61K 47/38; A61M 37/00
[52] U.S. Cl. .......................... 424/449; 424/448; 424/434
[58] Field of Search .................................... 424/449, 448, 424/434

[56] References Cited

U.S. PATENT DOCUMENTS

| | | | |
|---|---|---|---|
| 3,640,741 | 2/1972 | Etes | 106/170 |
| 3,996,934 | 12/1976 | Zaffaroni | 128/268 |
| 4,226,848 | 10/1980 | Nagai et al. | 424/19 |
| 4,250,163 | 2/1981 | Nagai et al. | 424/14 |
| 4,285,934 | 8/1981 | Tinnell | 424/148 |
| 4,286,592 | 9/1981 | Chandrasekaran | 128/260 |
| 4,292,299 | 9/1981 | Suzuki | 424/16 |
| 4,381,296 | 4/1983 | Tinnell | 424/148 |
| 4,517,173 | 5/1985 | Kizawa et al. | 424/16 |
| 4,518,721 | 5/1985 | Dhabhar et al. | 523/120 |
| 4,572,832 | 2/1986 | Kigasawa et al. | 424/19 |
| 4,668,232 | 5/1987 | Cordes et al. | 604/897 |
| 4,713,243 | 12/1987 | Schiraldi et al. | 424/151 |
| 4,715,369 | 12/1987 | Susuki et al. | 128/156 |
| 4,720,387 | 1/1988 | Sakamoto et al. | |
| 4,740,365 | 4/1988 | Yukimatsu et al. | 424/435 |
| 4,765,983 | 8/1988 | Takayanagi et al. | 424/434 |
| 4,867,970 | 9/1989 | Newsham et al. | 424/81 |
| 4,889,720 | 12/1989 | Konishi | 424/448 |
| 4,894,232 | 1/1990 | Reul et al. | 424/439 |
| 4,900,554 | 2/1990 | Yanagibashi et al. | 424/448 |
| 4,906,463 | 3/1990 | Cleary et al. | 424/78 |
| 4,915,948 | 4/1990 | Gallopo et al. | 424/435 |
| 4,990,339 | 2/1991 | Schull et al. | |
| 5,059,189 | 10/1991 | Cilento et al. | 604/307 |
| 5,064,654 | 11/1991 | Berner et al. | 424/448 |
| 5,081,157 | 1/1992 | Pomerantz | 514/781 |
| 5,081,158 | 1/1992 | Pomerantz | 514/781 |
| 5,116,621 | 5/1992 | Oji et al. | 424/445 |
| 5,137,729 | 8/1992 | Kuroya et al. | 424/435 |
| 5,192,802 | 3/1993 | Rencher | 514/535 |
| 5,196,202 | 3/1993 | Konishi | 424/448 |
| 5,298,258 | 3/1994 | Akemi et al. | 424/484 |
| 5,314,915 | 5/1994 | Rencher | 514/535 |
| 5,332,576 | 7/1994 | Mantelle | 424/443 |
| 5,462,749 | 10/1995 | Rencher | 424/484 |
| 5,466,465 | 11/1995 | Royds et al. | 424/449 |
| 5,505,956 | 4/1996 | Kim et al. | 424/448 |
| 5,780,047 | 7/1998 | Kamiya et al. | |

FOREIGN PATENT DOCUMENTS

| | | |
|---|---|---|
| 0050480 | 4/1982 | European Pat. Off. . |
| 0250187 | 12/1987 | European Pat. Off. . |
| 0381194 | 8/1990 | European Pat. Off. . |
| 0781546 | 7/1997 | European Pat. Off. . |
| 2497098 | 7/1982 | France . |
| 2582942 | 12/1986 | France . |
| 56/100714 | 8/1981 | Japan . |
| 0159604 | 10/1985 | Japan . |
| 0262422 | 4/1988 | Japan . |

*Primary Examiner*—Edward J. Webman
*Attorney, Agent, or Firm*—Morrison & Foerster LLP

[57] ABSTRACT

The present invention relates to water-soluble, bioerodable pharmaceutical delivery device for application to mucosal surfaces. The device comprises an adhesive layer and a non-adhesive backing layer, and the pharmaceutical may be provided in either or both layers. Upon application, the device adheres to the mucosal surface, providing drug delivery and protection to the treatment site.

27 Claims, No Drawings

BIOERODABLE FILM FOR DELIVERY OF PHARMACEUTICAL COMPOUNDS OF MUCOSAL SURFACES

This is a continuation of application Ser. No. 08/734,519 filed Oct. 18, 1996, now U.S. Pat. No. 5,800,832.

FIELD OF THE INVENTION

The present invention relates generally to a bioerodable, water-soluble pharmaceutical carrier which adheres to mucosal surfaces for the localized delivery of pharmaceutical compounds and protection of the treatment site.

BACKGROUND OF THE INVENTION

The localized treatment of body tissues, diseases, and wounds requires that the particular pharmaceutical component be maintained at the site of treatment for an effective period of time. Given the tendency of natural bodily fluids to rapidly wash away topically applied pharmaceutical components, the topical treatment of wet mucosal tissues has been problematic. In the mouth, saliva, natural replacement of the mucosal tissue, and eating, drinking, and speaking movements are some of the problems that have limited the effectiveness and residence time of pharmaceutical carriers.

Bioadhesive carriers are known in the art and include gels, pastes, tablets, and films. These products, however, may lack one or several of the preferred characteristic for an efficient and commercially acceptable pharmaceutical delivery device. Some characteristics which are preferred by users of bioadhesive carriers include water-erodability, ease of handling and application to the treatment site, and ease of comfort with minimal foreign body sensation. Other preferred characteristics for an effective and user-friendly product for the treatment of mucosal surfaces include the use of pharmaceutically approved components or materials; instantaneous adhesion to mucosal surface upon application; increased residence time for the protection of the affected tissue or the delivery of the pharmaceutical component; and ease of removal of the delivery device from the affected tissue or natural dissolution of the delivery device at the delivery site.

Bioadhesive gels which are used for application to mucosal tissues and especially the oral cavity are known in the art. For example, U.S. Pat. No. 5,192,802 describes a bioadhesive teething gel made from a blend of sodium carboxymethyl cellulose and xantham gum. The gel may also have potential use in the treatment of canker sores, fever blisters, and hemorrhoids. However, this type of pharmaceutical carrier has a very limited residence time, given that body fluids such as saliva quickly wash it away from the treatment site. Bioadhesive gels are also described in U.S. Pat. Nos. 5,314,915; 5,298,258; and 5,642,749. The gels described in those patents use an aqueous or oily medium and different types of bioadhesive and gelling agents.

Denture adhesive pastes are another type of bioadhesive product known in the art. However, these preparations are used primarily for their adhesive properties, to adhere dentures to the gums, rather than for the protection of tissue or for the topical delivery of pharmaceuticals, although drugs such as local anesthetics may be used in the paste for the relief of sore gums. U.S. Pat. Nos. 4,894,232 and 4,518,721 describe denture adhesive pastes. The '721 Patent describes a combination of sodium carboxymethyl cellulose and polyethylene oxide in polyethylene glycol.

Pastes have also been used as film protectants and as drug delivery systems. One such example having film forming and adhesive properties is the product commercialized under the name Orabase®-B, which is a thick gel or paste for the relief of mouth sores. Ingredients include guar gum, sodium carboxymethyl cellulose, tragacanth gum, and pectin. Even though it does provide numbing to the area of application, the film forming behavior and bioadhesion do not last. Thus, this product has a limited residence time.

Bioadhesive tablets are described in U.S. Pat. No. 4,915,948. The water-soluble bioadhesive material used in this device is a xanthan gum or a pectin combined with an adhesion enhancing material such as a polyol. Although residence time is improved with the use of bioadhesive tablets, they are not user friendly, especially when used in the oral cavity, given the unpleasant feelings associated with their solidity, bulkiness, and slow dissolution time. Bioadhesive tablets are also described in U.S. Pat. Nos. 4,226,848; 4,292,299; and 4,250,163, and are single layer or bilayer devices having an average thickness of 0.2 to 2.5 mm. The bioadhesive tablets described in these patents utilize a non-adhesive component such as cellulose ether, a bioadhesive component such as polyacrylic acid, sodium carboxymethyl cellulose, or polyvinylpyrrolidone, and a binder for tableting purposes. The cellulose derivatives may or may not be water-soluble. The claimed cellulosic materials in the '299 Patent are methyl cellulose, hydroxypropyl cellulose, and hydroxypropylmethyl cellulose.

The use of bandages or bioadhesive laminated films, which are thinner and flexible and therefore have a decreased foreign body sensation, is described in U.S. Pat. Nos. 3,996,934 and 4,286,592. These products are used to deliver drugs through the skin or mucous. The laminated films usually include an adhesive layer, a reservoir layer, and a backing layer. Bioadhesive devices designed to release drug through the skin at a given rate and over a period of time are usually not water soluble, and are not dissolved or washed away by bodily fluids.

In addition to film systems for the delivery of drug through the skin, film delivery systems for use on mucosal surfaces are also known. These types of systems, which are water-insoluble and usually in the form of laminated, extruded or composite films, are described in U.S. Pat. Nos. 4,517,173; 4,572,832; 4,713,243; 4,900,554; and 5,137,729. The '173 Patent describes and claims a membrane-adhering film consisting of at least three layers, including a pharmaceutical layer, a poor water soluble layer, and an intermediate layer. The pharmaceutical layer includes the drug and a cellulose derivative selected from hydroxypropyl cellulose, methyl cellulose, and hydroxypropyl methyl cellulose. The poor water soluble layer is made by the combination of one or more cellulose derivatives with a poor water soluble fatty acid, and the intermediate layer is made of cellulose derivatives. The '832 Patent relates to a soft film for buccal delivery, made by the combined use of a water soluble protein, a polyol, and a polyhydric alcohol such as cellulose and polysaccharides, and also teaches the use of coloring or flavoring agents. The '243 Patent describes a single or multi-layered bioadhesive thin film made from 40–95% water soluble hydroxypropyl cellulose, 5–60% water-insoluble ethylene oxide, 0–10% water-insoluble ethyl cellulose, propyl cellulose, polyethylene, or polypropylene, and a medicament. The films are three-layered laminates and include a bioadhesive layer, a reservoir layer, and a non water-soluble outer protective layer. The '729 Patent teaches a soft adhesive film applicable to the oral mucosa containing a systemic drug and comprising a mixture of a vinyl acetate non water-soluble homopolymer, an acrylic acid polymer, and a cellulose derivative. Finally, the '554 Patent describes a device for use in the oral cavity having an adhesive layer including a mixture of an acrylic acid polymer, a water-insoluble cellulose derivate, and a pharmaceutical preparation, and a water-insoluble or sparingly soluble backing layer. The adhesive layer contains the pharmaceutical, and upon application to the mucosal surface, delivers the drug. The '554 Patent also states that "it is impossible to achieve an adhesive device for application to body tissue without all three components, that is, acrylic acid polymer, water insoluble cellulose derivative and a water insoluble or sparingly soluble backing layer."

The previous examples of thin films to be applied in the oral cavity by adhesion onto the mucosal tissues all utilize polymers which are water-insoluble by nature or which are made water-insoluble by crosslinking, and claim a long residence time. They are satisfactory but do not provide a water soluble device with good adhesive properties. Therefore, following application for an expected period of time and the release of an amount of drug, the thin films made by water insoluble polymers must be peeled off of the site of application.

SUMMARY OF THE INVENTION

The present invention relates to a novel water-soluble pharmaceutical carrier device for application to mucosal surfaces to provide protection of and delivery of pharmaceutical to the site of application, surrounding tissues, and other bodily fluids, having an effective residence time, with minimal discomfort and ease of use. In one embodiment, the device includes a mucoadhesive bilayer film disk which is water-soluble and bioerodable. In one embodiment, the pharmaceutical delivery device comprises a bilayer film disk having an adhesive layer and a backing layer, both water-soluble, having the pharmaceutical in either or both layers. The adhesive layer comprises a film forming polymer such as hydroxyethyl cellulose, hydroxyproyl cellulose, hydroxypropylmethyl cellulose, or hydroxyethyl methyl cellulose, alone or in combination, and a bioadhesive polymer such as polyacrylic acid, polyvinyl pyrrolidone, or sodium carboxymethyl cellulose, alone or in combination. The nonadhesive backing layer comprises hydroxyethyl cellulose, hydroxypropyl cellulose, hydroxyethylmethyl cellulose, hydroxypropylmethyl cellulose, polyvinyl alcohol, polyethylene glycol, polyethylene oxide, or ethylene oxide-propylene oxide co-polymers, alone or in combination. Methods for treating mucosal surfaces, surrounding tissues, and bodily fluids, by applying the bilayer film to the treatment site for drug delivery and protection of the site of application, are also provided.

DETAILED DESCRIPTION OF THE INVENTION

In the present invention, a novel water soluble, bioerodable pharmaceutical device which adheres to mucosal surfaces is provided. The present invention finds particular use in the localized treatment of body tissues, diseases, or wounds which may have moist surfaces and which are susceptible to bodily fluids, such as the mouth, the vagina, or other types of mucosal surfaces. The device carries a pharmaceutical, and upon application and adherence to the mucosal surface, offers a layer of protection and delivers the pharmaceutical to the treatment site, the surrounding tissues, and other bodily fluids. The device provides an appropriate residence time for effective drug delivery at the treatment site, given the control of solubilization in aqueous solution or bodily fluids such as saliva, and the slow, natural dissolution of the film concomitant to the delivery. In one embodiment, the pharmaceutical delivery device comprises a bilayer film disk having an adhesive layer and a backing layer, both water-soluble, having the pharmaceutical in either or both layers.

Unlike bioadhesive gels and pastes known in the art, which have a very limited residence time, given the tendency of bodily fluids such as saliva to wash away the gel from the treatment site, the present invention offers an increased residence time because of its filmy consistency and components. A typical residence time for an aqueous gel or paste, such as Orajel®, Orabase®, or Kanka® is a few minutes. This short residence time is a consequence of a limited or poor adhesion. In a typical aqueous gel, the mucoadhesive components are either in solution, suspension, or swollen. Once applied to the mucosal surface, however, the water based gel does not instantaneously penetrate the lipophilic mucosal surface. The composition and water affinity of these gels results in a tendency to quickly mix with the saliva, rapidly pulling away the different components of the gel, and limiting the residence time. The same tendency is expected with pastes, the increase in viscosity only slightly delaying the timing. The present invention, by its solid form and its instantaneous adhesion to the mucosal surface, allows a lasting contact, a consequence of the entanglement of polymer chains and glycoproteins of the mucosal tissue which assures adhesion. Dissolution kinetics in the saliva and other aqueous media are influenced by the physical state of the device. While a gel or solution will readily mix with saliva and/or other bodily fluids, a solid form such as a crystalline, film, or precipitate of the same or similar composition is expected to dissolve more slowly.

Also, unlike the bioadhesive tablets which are known in the art, the pharmaceutical device of the present invention minimizes the discomfort associated with application of a foreign substance for a period of time sufficient to provide effective drug delivery to the treatment site. Although bioadhesive tablets do offer effective residence time, users of bioadhesive tablets experience unpleasant sensations due to their solidity, bulkiness, and slow dissolution time if erodable, especially when used in the oral cavity. Moreover, the typical thickness of bioadhesive tablets, which may or may not be water soluble, is a couple of millimeters, and because of their thickness, the preferred site of application is on the upper gingival area. This site is quite satisfactory for the systemic delivery of an active component, but may not be as satisfactory for local delivery. The device of the present invention offers the advantages of an effective residence time with minimal discomfort and ease of use, and is an appropriate vehicle for the local as well as systemic delivery of pharmaceutical, given its thinner, flexible form.

Finally, unlike the film systems known in the art which are used to deliver pharmaceutical through the skin or mucous, the device of the present invention is made of water-soluble components and is bioerodable. The use of water-soluble components allows the device to dissolve over a period of time, with natural bodily fluids slowly dissolving and eroding away the carrier, while the pharmaceutical remains at the application site. Unlike bandages and other non-water-soluble film systems, the user of the present invention does not have to remove the device following treatment. Nor does the user experience the sensation of the presence of a foreign object at the mucosal surface or within the body cavity, given that upon application, water absorption softens the device, and over time, the device slowly dissolves or erodes away.

The residence time of the device of the present invention depends on the dissolution rate of the water-soluble polymers used. The dissolution rate may be adjusted by mixing together chemically different polymers, such as hydroxyethyl cellulose and hydroxypropyl cellulose; by using different molecular weight grades of the same polymer, such as mixing low and medium molecular weight hydroxyethyl cellulose; by using crosslinking agents such as glyoxal with polymers such as hydroxyethyl cellulose for partial crosslinking; or by post-treatment irradiation or curing, which may alter the physical state of the film, including its crystallinity or phase transition, once obtained. These strategies might be employed alone or in combination in order to modify the dissolution kinetics of the device, without suppressing the water solubility characteristics of the component materials.

Upon application, the pharmaceutical delivery device adheres to the mucosal surface and holds in place. Water absorption softens the device quickly, diminishing and eliminating the foreign body sensation. As the device rests on the mucosal surface, delivery of the drug is provided. Residence times may vary, depending on the formulation and materials used, but may be modulated between a few minutes to several hours. Residence times which may be achieved with this invention include 30 minutes to about 3 or 4 hours. A preferred residence time for effective drug delivery is about 1 to 2 hours. In addition to providing drug delivery, once the device adheres to the mucosal surface, it also provides protection to the treatment site, acting as an erodable band aid.

In one embodiment, the present invention comprises a film disk having two layers—an adhesive layer and a non-adhesive backing layer—which are both water soluble and made of pharmacologically-approved materials. The pharmaceutical component may be included in either layer, although preferably, it is included in the adhesive layer, which is closest to the treatment site and which will have a slower dissolution time, given that the backing layer protects the interior, adhesive layer and will dissolve first.

The adhesive layer may comprise at least one film-forming water-soluble polymer, usually a cellulose derivative (the "film-forming polymer") and at least one pharmacologically acceptable polymer known for its bioadhesive capabilities (the "bioadhesive polymer"). The film forming polymer may comprise hydroxyethyl cellulose, hydroxypropyl cellulose, hydroxypropylmethyl cellulose, hydroxyethylmethyl cellulose, or a combination thereof. Preferably, the film-forming polymer comprises hydroxyethyl cellulose. Preferably, in the case of hydroxyethyl cellulose, the average molecular weight (Mw estimated from intrinsic viscosity measurements) is in the range $10^2$ to $10^6$ and more preferably in the range $10^3$ to $10^5$, while in the case of hydroxypropyl cellulose, the average molecular weight (Mw obtained from size exclusion chromatography measurements) is in the range $50 \times 10^3$ to $1.5 \times 10^6$, and more preferably between $80 \times 10^3$ to $5 \times 10^5$. The film-forming, polymer may be crosslinked or plasticized in order to alter its dissolution kinetics.

The bioadhesive polymer of the adhesive layer may comprise polyacrylic acid (PAA), which may or may not be partially crosslinked, sodium carboxymethyl cellulose (NaCMC), and polyvinylpyrrolidone (PVP), or combinations thereof. These bioadhesive polymers are preferred because they have good and instantaneous mucoadhesive properties in a dry, film state. In the case of sodium carboxymethyl cellulose, typical average molecular weights comprise 50,000 to 700,000, and preferably 60,000 to 500,000, with a degree of substitution of 0.7. The substitution range varies between 0.5 and 1.5, and preferably between 0.6 and 0.9. The polyvinyl pyrrolidone can be characterized according to its average molecular weight and comprises between 5,000 and 150,000, preferably between 10,000 and 100,000. The simultaneous use of PAA with some grades of PVP may result in the precipitation of one or both components. This precipitation may not be ideal to obtain a homogenous layer and may slightly alter the overall adhesive properties of the device.

The adhesion properties of the present invention are the result of the entanglement of polymer chains and interactions with glycoproteins of the mucosal surface. The chemical nature of the bioadhesive polymers, including chain and side groups and crosslinking agents, generates interactions between the mucosal constituents and the polymer or polymers, such as physical entanglement, Van der Waals interactions, and hydrogen bonding. Given that the composition of mucosal tissues differs from one individual to another and changes naturally over time, the use of a combination of bioadhesive polymers or the use of a combination of different grades of the same polymer is preferred. The use of a combination of at least two bioadhesive polymers maximizes the adhesion capabilities of the device, although use of a single bioadhesive polymer is effective as well.

The ratio of the bioadhesive polymer to the film-forming polymer in the adhesive layer may vary, depending on the type of pharmaceutical and the amount of pharmaceutical to be used. However, the content of combined components in the adhesive layer is between 5 and 95% by weight, preferably between 10 and 80% by weight. In terms of weight percent of the different bioadhesive polymers PAA, NaCMC, and PVP, some examples are provided below. Preferred combinations include PAA and NaCMC, NaCMC and PVP, or PAA and PVP, and also include the use of different grades of the same polymer.

The non adhesive backing layer may comprise a water-soluble, film-forming pharmaceutically acceptable polymer such as hydroxyethyl cellulose, hydroxypropyl cellulose, hydroxypropylmethyl cellulose, hydroxyethylmethyl cellulose, polyvinylalcohol, polyethylene glycol, polyethylene oxide, ethylene oxide-propylene oxide co-polymers, or a combination thereof. The backing, layer component may or may not be crosslinked. In one embodiment, the preferred backing layer component comprises hydroxyethyl cellulose or hydroxypropyl cellulose, and more preferably comprises hydroxyethyl cellulose. Preferably, in the case of hydroxyethyl cellulose, the average molecular weight (Mw estimated from intrinsic viscosity measurements) is in the range $10^2$ to $10^6$, and more preferably in the range $10^3$ to $10^5$, while in the case of hydroxypropyl cellulose, the average molecular weight (Mw obtained from size exclusion chromatography measurements) is in the range of $50 \times 10^3$ to $1.5 \times 10^6$ and more preferably from $80 \times 10^3$ to $5 \times 10^5$.

Combinations of different polymers or similar polymers with definite molecular weight characteristics may be used in order to achieve preferred film forming capabilities, mechanical properties, and kinetics of dissolution. Some combinations for use in the invention are provided in the examples below and may include ¾ of hydroxyethyl cellulose and ¼ of hydroxypropyl cellulose; ⅘ of low molecular weight hydroxyethyl cellulose and ⅕ of medium molecular weight hydroxyethyl cellulose; and ⅚ of low molecular weight hydroxyethyl cellulose and ⅙ of high molecular weight hydroxyethyl cellulose. In order to modify the water dissolution kinetics of the backing layer without resulting in a non-water soluble material, partial and limited crosslinking may be used. Crosslinking agents known in the art are appropriate for use in the invention and may include glyoxal, propylene glycol, glycerol, dihydroxy-polyethylene glycol of different sizes, and butylene glycol. The amount of crosslinking agent used may vary, depending on the particular polymers and crosslinking agent, but should not exceed 5% molar equivalent of the polymeric material, and preferably comprises 0 to 3% molar equivalent of the polymeric material. Dissolution characteristics may be adjusted to modify the residence time and the release profile of a drug when included in the backing layer.

The pharmaceutical component of the present invention may comprise a single pharmaceutical or a combination of pharmaceuticals, which may be incorporated in the adhesive layer, the backing layer, or both. Pharmaceuticals which may be used, either alone or in combination, include anti-inflammatory analgesic agents, steroidal anti-inflammatory agents, antihistamines, local anesthetics, bactericides and disinfectants, vasoconstrictors, hemostatics, chemotherapeutic drugs, antibiotics, keratolytics, cauterizing agents, and antiviral drugs.

Examples of anti-inflammatory analgesic agents include acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexarnac, piroxicam, phenylbutazone, oxyphenbutazone, clofezone, pentazocine, mepirizole, tiaramide hydrochloride, etc. Examples of steroidal anti-inflammatory agents include hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, etc.

Examples of antihistamines include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, etc. Examples of local anesthetics include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, etc.

Examples of bactericides and disinfectants include thimerosal, phenol, thymol, benzalkonium chloride, benzethonium chloride, chlorhexidine, povidone iode, cetylpyridinium chloride, eugenol, trimethylammonium bromide, etc. Examples of vasoconstrictors include naphazoline nitrate, tetrahydrozoline hydrochloride, oxymetazoline hydrochloride, phenylephrine hydrochloride, tramazoline hydrochloride, etc. Examples of hemostatics include thrombin, phytonadione, protamine sulfate, aminocaproic acid, tranexamic acid, carbazochrome, carbaxochrome sodium sulfanate, rutin, hesperidin, etc.

Examples of chemotherapeutic drugs include sulfamine, sulfathiazole, sulfadiazine, homosulfamine, sulfisoxazole, sulfisomidine, sulfamethizole, nitrofurazone, etc. Examples of antibiotics include penicillin, meticillin, oxacillin, cefalotin, cefalordin, erythromcycin, lincomycin, tetracycline, chlortetracycline, oxytetracycline, metacycline, chloramphenicol, kanamycin, streptomycin, gentamicin, bacitracin, cycloserine, etc.

Examples of keratolytics include salicylic acid, podophyllum resin, podolifox, and cantharidin. Examples of cauterizing agents include the chloroacetic acids and silver nitrate. Examples of antiviral drugs include protease inhibitors, thymadine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

The amount of active pharmaceutical (s) to be used depends on the desired treatment strength, although preferably, the pharmaceutical component comprises 0.001 to 30% by weight of the device, and more preferably between 0.005 and 20% by weight.

Plasticizers, flavoring and coloring agents, and preservatives may also be included in the pharmaceutical delivery device of the present invention in the adhesive layer, the backing layer, or both. Preferably, these components comprise no more than 1% of the final weight of the device, but the amount may vary depending on the drug or other components.

The thickness of the device may vary, depending on the thickness of each of the layers. Preferably, the bilayer thickness ranges from 0.05 mm to 1 mm, and more preferably from 0.1 to 0.5 mm. The thickness of each layer may vary from 10 to 90% of the overall thickness of the bilayer device, and preferably varies from 30 to 60%. Thus, the preferred thickness of each layer may vary from 0.01 mm to 0.9 mm, and more preferably from 0.03 to 0.6 mm.

The pharmaceutical delivery device of the present invention may be prepared by numerous methods known in the art. In one embodiment, the components are dissolved in the appropriate solvent or combination of solvents to prepare a solution. Solvents for use in the present invention may comprise water, methanol, ethanol, or low alkyl alcohols such as isopropyl alcohol, acetone, methyl ethyl cetone, heptane, or dichloroethane, alone or combination. The final solvent content or residual solvent content in the film may be the result of either or both layers. The solvent may also be used as a plasticizer or dissolution-rate-modifying agent.

Each solution is then coated onto a substrate. Eventually, one of the components might be in suspension. Each solution is casted and processed into a thin film by techniques known in the art, such as by film dipping, film coating, film casting, spin coating, or spray drying using the appropriate substrate. The thin film is then dried. The drying step can be accomplished in any type of oven. However) the solvent residual depends on the drying procedure. The film layers may be filmed independently and then laminated together or may be filmed one on the top of the other.

The film obtained after the two layers have been laminated together or coated on top of each other may be cut into any type of shape, for application to the mucosal tissue. Some shapes include disks, ellipses, squares, rectangles, and parallepipedes.

Methods for treating mucosal surfaces, surrounding tissues, and bodily fluids for localized and systemic drug delivery are also provided. In one embodiment, the method comprises applying an adherent film of the invention to the treatment site in order to provide protection to the treatment site and drug delivery. The adherent film may comprise any of the bilayer devices provided in herein. In a preferred embodiment, the method comprises application of a bilayer pharmaceutical carrier device having a first adhesive layer and a second non-adhesive backing layer as described above, each layer having a thickness of from 0.01 mm to 0.9 mm. The pharmaceutical or combination of pharmaceuticals may be present in the adhesive layer, the non-adhesive backing layer, or both layers.

EXAMPLE 1

A 100 ml solution for the non-adhesive backing layer was made using 87.98% by weight water USP, 0.02% by weight FD&C red 40 dye, and 12% by weight hydroxyethyl cellulose (Mw $9 \times 10^4$). Using a Werner Mathis Labcoater, the substrate (Mylar 1000D or other polyester films such as 3M ScotchPak 1022) was set. 90 ml of the backing layer solution was set in front of a knife over roll with an opening of 1.5 mm. The solution was then casted on a glass substrate and film dried for 8–9 min. at 130° C. Following the drying step, a 0.14 mm thick redish film was the result.

Using this procedure, the film may be easily peeled off the substrate after drying, or may be left on the substrate and rolled, to be laminated later, or for use as a substrate for the adhesive layer.

EXAMPLE 2

A 100 ml solution for the non-adhesive backing layer was made using 94.98% by weight water USP, 0.02% by weight FD&C red 40 dye, and 5% by weight hydroxypropyl cellulose. The procedure of example 1 was used, resulting in a 0.16 mm thick film.

EXAMPLE 3

A 100 ml solution for the non-adhesive backing layer was made using 84.98% by weight water USP, 0.02% by weight FD&C red 40 dye, 12% by weight hydroxyethyl cellulose, and 3% by weight hydroxypropyl cellulose. Here, the overall polymeric material was at a 15% concentration in solution. The mixture of two different types of polymeric materials modified the overall mechanical properties and dissolution kinetics characteristics of the backing film. The solution was then casted on a polyester substrate and dried overnight at 90° C. The opening of the knife was set at 3 mm, resulting in a 0.3 mm thick film.

EXAMPLE 4

A 100 ml solution for the non-adhesive backing layer was made using 87.98% by weight water USP, 0.02% by weight FD&C red 40 dye, 10% by weight hydroxyethyl cellulose (Mw $9 \times 10^4$), and 2% by weight hydroxyethyl cellulose (Mw $7 \times 10^5$). Here, the mixture of two different types of hydroxyethyl cellulose modified the mechanical properties and dissolution kinetics of the backing film. The solution was then casted on a polyester substrate and dried for 12 min. at 135° C. The opening of the knife was set at 3 mm, resulting in a 0.27 mm thick film.

EXAMPLE 5

A 100 ml solution for the non-adhesive backing layer was made using 87.98% by weight water USP, 0.02% by weight FD&C red 40 dye, 11.75% by weight hydroxyethyl cellulose (Mw $9 \times 10^4$), and 0.25% by weight hydroxyethyl cellulose (Mw $1.3 \times 10^6$). The procedure of Example 1 was used, resulting in a 0.14 mm thick film.

Here, the mixture of two different grades of hydroxyethyl cellulose modified the mechanical properties and dissolution kinetics of the backing film. The ratio may be used to adjust the dissolution pattern and residence time of the bioadhesive disk. Compared to the backing layer of Example 1, which was made of 12% by weight hydroxyethyl cellulose (Mw $9 \times 10^4$), and which had a dissolution time of about 21 minutes (See Table 2), the backing layer of this Example, made from a combination of two grades of hydroxyethyl cellulose, had a dissolution tire of about 69 minutes (See Table 2).

EXAMPLE 6

A 100 ml solution for the non-adhesive backing layer was made using 87.98% by weight water USP, 0.02% by weight FD&C red 40 dye, 11.95% by weight hydroxyethyl cellulose (Mw $9 \times 10^4$), and 0.05% by weight of 40% glyoxal aqueous solution. The procedure of Example 1 was used, resulting in a 0.13 mm film.

Here, the glyoxal acted as a crosslinking agent, inducing a slow down in the dissolution kinetics of the backing film. Compared to the backing layer of Example 1, which had no glyoxal and which had a dissolution time of about 21 minutes (See Table 2), the backing layer of this Example, which incorporated glyoxal, had a dissolution time of about 57 minutes (See Table 2).

EXAMPLE 7

A 100 ml solution for the non-adhesive backing layer was made using 87.98% by weight water USP, 0.02% by weight FD&C red 40 dye, 11.8% by weight hydroxyethyl cellulose, 0.1% by weight of 40% glyoxal aqueous solution, and 0.1% sweet peppermint flavor. Here, as in Example 6, the glyoxal acted as a crosslinking agent, inducing a slow down in the dissolution kinetics of the backing film, compared with a backing layer with no glyoxal. The sweet peppermint was added as a flavoring agent.

EXAMPLE 8

As described in example 1, the solutions of examples 5, 6 and 7 were each casted on a polyester substrate. Instead of using a knife, a meier's bar was used to coat the substrate. The films were dried overnight at 90° C. The dried films were thicker, having a thickness of about 0.17 mm.

EXAMPLE 9

The solution of Example 1 was prepared in a beaker. A microslide was then dipped quickly into the solution until it was fully immersed, removed from the solution, and left at room temperature for about 1 hour. The microslide was then dried overnight at 90° C. The resulting film was heterogenous and had an average thickness of about 0.2 mm.

EXAMPLE 10

A 100 ml solution for the non-adhesive backing layer was made using 84% by weight water USP, 0.02% by weight FD&C red 40 dye, 11% by weight hydroxyethyl cellulose (Mw $9 \times 10^4$), 1% by weight hydroxyethyl cellulose (Mw $7 \times 10^5$), 0.1% by weight of a 40% glyoxal aqueous solution, 3% by weight glyoxal, and 1% by weight menthol. Here, the glyoxal acted as a crosslinking agent, inducing a slow down in the dissolution kinetics of the backing film. Also, the mixture of two different grades of hydroxyethyl cellulose was used to achieve slow release of the menthol. The film was coated on a polyester film as previously described.

EXAMPLE 11

A 100 ml solution for the adhesive layer was made using 88.6% by weight water USP, 1.8% by weight hydroxyethyl cellulose, Natrosol® 99-250 L NF (Aqualon), 2.6% by weight polyacrylic acid, Noveon® AA1 USP (BF Goodrich), 4.5% sodium carboxymethyl cellulose, cellulose gum 7 LF PH (Aqualon), and 2.5% by weight dyclonine HCl. Upon mixing, a suspension was formed.

Here, dyclonine HCl may be easily substituted with any other active pharmaceutical component. However, chemical characteristics of the active pharmaceutical, such as solubility, counter ions, and melting point, might require minor modifications of the overall process, such as dissolution in a particular solvent, changing the temperature of the solution, etc. The next example illustrates one slight modification.

EXAMPLE 12

A 100 ml solution for the adhesive layer was made using 74.6% by weight water USP, 1.8% by weight hydroxyethyl cellulose, 2.6% by weight polyacrylic acid, 4.5% sodium carboxymethyl cellulose, 2.5% by weight benzocaine, and 14% by weight ethyl alcohol. The use of benzocaine as the active pharmaceutical required that it first be dissolved in ethyl alcohol, given that benzocaine is more soluble in alcohol than water.

In the final solution, the benzocaine tends to precipitate in the form of a very fine powder. However, the film characteristics and bioadhesive properties remain intact.

EXAMPLE 13

A 100 ml solution for the adhesive layer was made using 91% by weight water USP, 2% by weight hydroxyethyl cellulose, 2.5% by weight polyacrylic acid, and 4.5% sodium carboxymethyl cellulose. The composition of the adhesive layer may be modified and may vary according the ranges described in Table 1 below:

TABLE 1

| Item # | % w | Material |
| --- | --- | --- |
| 1 | 60 to 99.5 | Water USP |
| 2 | 0.05 to 5 | Hydroxyethyl cellulose |
| 3 | 0.5 to 10 | Polyacrylic acid |
| 4 | 0.0 to 15 | Sodium Carboxymethyl cellulose |
| 5 | 0 to 10 | Polyvinyl pyrrolidone |

The relative part of each components depends of the chemical compatibility of the components and the residence time to be obtained.

EXAMPLE 14

A 100 ml solution for the adhesive layer was made using 90% by weight water USP, 1% by weight butacaine sulfate, 2% by weight hydroxyethyl cellulose, 2.5% by weight polyvinyl pyrrolidone, and 4.5% by weight sodium carboxymethyl cellulose. The solution was coated using a knife over roll on a Mylar substrate.

EXAMPLE 15

A 100 ml solution for the adhesive layer was made. The total composition of the solution was 48.6% water, 40% ethyl alcohol, 1.8% hydroxyethyl cellulose, 2.6% polyacrylic acid, 4.5% sodium carboxymethyl cellulose, and 2.5% dyclonine HCl. Here, however, the dyclonine HCl was first solubilized in 40 ml ethyl alcohol, and then, 48.6 ml of water were added to the dyclonine HCl/ethyl alcohol solution, followed by the addition of the other components.

The use of ethyl alcohol as an additional solvent resulted in a suspension which was slightly more viscous than that of Example 11, which used water as the only solvent.

EXAMPLE 16

Following the procedure of Example 12, a 100 ml solution for the adhesive layer was prepared. The solution was then coated following the procedure used in Example 1. The resulting film was 0.12 mm thick.

EXAMPLE 17

Following the procedure of Example 12, a 100 ml solution for the adhesive layer was prepared. The solution was coated on top of a backing film prepared according to Example 1. The opening of the knife was adjusted, taking into account the thickness of the backing film. After coating, the bilayer film was dried at 130° C. for 15 minutes. A 0.27 mm bilayer film was formed.

EXAMPLE 18

Following the procedure of Example 14, a bioadhesive film was prepared, except that the film was not fully dried. A backing film was prepared according to Example 1. The backing film was peeled off of its substrate and laminated on top of the bioadhesive film while still moist, and pressure was applied to seal the two films together. The pressure applied on the films resulted in a good interfacial adhesion. A 0.38 mm bilayer film was formed.

EXAMPLE 19

Following the procedure of Example 1, several solutions for backing films were prepared according to the compositions of Table 2 below. Following film formation, ½ inch disks were die cut and set on a double-sided tape. The tape was then positioned on a micro slide. The kinetics of dissolution were evaluated in water: the slide was plunged into a 100 ml beaker of water stirred at a constant speed of 50 rpm. The time for dissolution was measured from the moment the disk was fully immersed in the beaker of water. Percentages (%) refer to the concentration in solution.

TABLE 2

| Composition | Weight (mg)/Thickness (mm) | Dissolution Time (min.) |
| --- | --- | --- |
| 12% HEC (Mw $9 \times 10^4$) | 17.1/0.14 | 21 |
| 10% HEC (Mw $9 \times 10^4$) and 2% HEC (Mw $7 \times 10^5$) | 16.9/0.13 | 37 |
| 9% HEC (Mw $9 \times 10^4$) and 3% HEC (Mw $7 \times 10^5$) | 17/0.14 | 75 |
| 11.75% HEC ((Mw $9 \times 10^4$) and 0.25% HEC (Mw $1.3 \times 10^6$) | 17.1/0.14 | 69 |
| 11.95% HEC ((Mw $9 \times 10^4$) and 0.05% glyoxal (40% aq. sol.) | 17.2/0.13 | 57 |
| 11.99% HEC ((Mw $9 \times 10^4$) and 0.01% propylene glycol | 17.3/0.14 | 65 |

The results demonstrate that the dissolution lime varies, depending on the components of the formulation, assuming a similar surface state for each sample. Although water does not mimic the exact composition of saliva, and this experiment cannot precisely replicate in vivo residence times, the experiment provides an in vitro comparison of dissolution times of various compositions for use in practicing the present invention.

EXAMPLE 20

½ inch diameter disks having a thickness of between 0.19 and 0.21 mm were administered to six healthy volunteers.

The backing layer was prepared according to Example 1, and the adhesive layer was prepared according to Example 15, some containing dyclonine HCl as the active pharmaceutical component, and others containing benzocaine as a substitute. The adhesive layer was coated on top of the backing layer, forming a bilayer disk. The bilayer disk was set in the mouth, and the time for dissolution was measured from the moment the disk was set in place.

Participants were asked to evaluate the disk's handling and numbing effect on a scale of 0 to 3, with 3 being very good, 2 good, 1 fair, and 0 poor. Participants also evaluated the time necessary for adhesion; the residence time; the foreign body sensation, if any, and its duration; and the dissolution of the disk. Finally, participants were asked to evaluate the overall effectiveness of the disk and their overall impression, as well as which pharmaceutical component, dyclonine HCl (D) or benzocaine (B), they preferred. The results are described in Table 3 below.

TABLE 3

| No. | Handling | Adhesion | Residence Time | Foreign Body Sensation | Numbing | Dissolution | Efficiency | Overall | Pharmaceutical Pref. |
|---|---|---|---|---|---|---|---|---|---|
| 1 | 3 | instant | ~1 hr | <5 min. | 3 | did not notice | + | + | B |
| 2 | 2 | instant | 1 hr | <5 min. | 3 | did not notice | + | + | B |
| 3 | 3 | instant | 45 min. | no | 2 | did not notice | + | + | D |
| 4 | 3 | instant | 45 min. | no | 2 | at the end | + | − | D |
| 5 | 2 | instant | 30 min. | <5 min. | 3 | at the end | + | + | D |
| 6 | 1 | difficult | ~15 min. | <5 min. | 2 | did not notice | − | − | D |

The results demonstrate that although the handling of the disk may be difficult for first time users, the adhesion is instantaneous, there is only a minor foreign body sensation which disappears after a couple minutes upon swelling of the disk, and numbing is effective.

Those skilled in the art will recognize that, while specific embodiments have been illustrated and described, various modifications and changes may be made without departing from the spirit and scope of the invention.

What is claimed is:

1. A biodegradable, water-soluble pharmaceutical carrier device comprising a layered flexible film having a first water-soluble adhesive layer to be placed in contact with the mucosal surface and a second, water-soluble non-adhesive backing layer, and a pharmaceutical or combination of pharmaceuticals incorporated with said first or second layer, wherein said first water-soluble adhesive layer comprises hydroxyethyl cellulose, polyacrylic acid, and sodium carboxymethyl cellulose; and said second water-soluble non-adhesive backing layer comprises hydroxyethyl cellulose.

2. The pharmaceutical carrier device of claim 1, wherein said pharmaceutical or combination of pharmaceuticals comprises an anti-inflammatory analgesic agent.

3. The pharmaceutical carrier device of claim 2, wherein said anti-inflammatory analgesic agent is acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, or tiaramide hydrochloride.

4. The pharmaceutical carrier device of claim 1, wherein said pharmaceutical or combination of pharmaceuticals comprises an steroidal anti-inflammatory agent.

5. The pharmaceutical carrier device of claim 4, wherein said steroidal anti-inflammatory agent is hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, or beclomethasone diproprionate.

6. The pharmaceutical carrier device of claim 1, wherein said pharmaceutical or combination of pharmaceuticals comprises a local anesthetic other than dyclonine HCl.

7. The pharmaceutical carrier device of claim 6, wherein said local anesthetic is dibucaine hydrochloride, dibucaine, lidocaine hydrochloride, lidocaine, benzocaine, p-buthylaminobenzoic acid 2-(di-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, dyclonine, or piperocaine hydrochloride.

8. The pharmaceutical carrier device of claim 1, wherein said pharmaceutical or combination of pharmaceuticals comprises an antihistamine.

9. The pharmaceutical carrier device of claim 8, wherein said antihistamine is diphenhydramine hydrochloride, diphenhydramine salicylate, diphenhydramine, chlorpheniramine hydrochloride, chlorpheniramine malcate isothipendyl hydrochloride, tripelennamine hydrochloride, promethazine hydrochloride, or methdilazine hydrochloride.

10. The pharmaceutical carrier device of claim 1, wherein said pharmaceutical or combination of pharmaceuticals comprises a bactericide.

11. The pharmaceutical carrier device of claim 10, wherein said bactericide is thimerosal, phenol, thymol, benzalkonium chloride, benzethonium chloride, chlorhexidine, povidone iodide, cetylpyridinium chloride, eugenol, or trimethylammonium bromide.

12. The pharmaceutical carrier device of claim 1, wherein said pharmaceutical or combination of pharmaceuticals comprises a vasoconstrictor.

13. The pharmaceutical carrier device of claim 12, wherein said vasoconstrictor is naphazoline nitrate, tetrahydrozoline hydrochloride, oxymetazoline hydrochloride, phenylephrine hydrochloride, or tramazoline hydrochloride.

14. The pharmaceutical carrier device of claim 1, wherein said pharmaceutical or combination of pharmaceuticals comprises a hemostatic agent.

15. The pharmaceutical carrier device of claim 14, wherein said hemostatic agent is thrombin, phytonadione, protamine sulfate, aminocaproic acid, tranexamic acid, carbazochrome, carbaxochrome sodium sulfanate, rutin, or hesperidin.

16. The pharmaceutical carrier device of claim 1, wherein said pharmaceutical or combination of pharmaceuticals comprises a chemotherapeutic agent.

17. The pharmaceutical carrier device of claim 16, wherein said chemotherapeutic agent is sulfamine, sulfathiazole, sulfadiazine, homosulfamine, sulfisoxazole, sulfisomidine, sulfamethizole, or nitrofurazone.

18. The pharmaceutical carrier device of claim 1, wherein said pharmaceutical or combination of pharmaceuticals comprises an antibiotic.

19. The pharmaceutical carrier device of claim 18, wherein said antibiotic is penicillin, meticillin, oxacillin, cefalotin, cefalordin, erythromcycin, lincomycin, tetracycline, chlortetracycline, oxytetracycline, metacycline, chloramphenicol, kanamycin, streptomycin, gentamicin, bacitracin, or cycloserine.

20. The pharmaceutical carrier device of claim 1, wherein said pharmaceutical or combination of pharmaceuticals comprises a keratolytic agent.

21. The pharmaceutical carrier device of claim 20, wherein said keratolytic agent is salicylic acid, podophyllum resin, podolifox, or cantharidin.

22. The pharmaceutical carrier device of claim 1, wherein said pharmaceutical or combination of pharmaceuticals comprises a cauterizing agent.

23. The pharmaceutical carrier device of claim 22, wherein said cauterizing agent is chloroacetic acid or silver nitrate.

24. The pharmaceutical carrier device of claim 1, wherein said pharmaceutical or combination of pharmaceuticals comprises an antiviral.

25. The pharmaceutical carrier device of claim 24, wherein said antiviral is a protease inhibitor, a thymadine kinase inhibitor, a sugar synthesis inhibitor, a glycoprotein synthesis inhibitor, a structural protein synthesis inhibitor, an attachment inhibitor, an adsorption inhibitor, a nucleoside analog, acyclovir, penciclovir, valacyclovir, or ganciclovir.

26. The pharmaceutical carrier device of claim 1, wherein the pharmaceutical comprises between about 0.001 percent and about 30 percent by weight of the pharmaceutical carrier device.

27. The pharmaceutical carrier device of claim 26, wherein the pharmaceutical comprises between about 0.005 percent and about 20 percent by weight of the pharmaceutical carrier device.

* * * * *

UNITED STATES PATENT AND TRADEMARK OFFICE
CERTIFICATE OF CORRECTION

PATENT NO. : 6,159,498
DATED : December 12, 2000
INVENTOR(S) : Gilles H. Tapolsky and David W. Osborne It is certified that error appears in the above-identified patent and that said Letters Patent is hereby corrected as shown below:

<u>Title page,</u>
Under Item [54], replace the title with:
-- BIOERODABLE FILM FOR DELIVERY OF PHARMACEUTICAL COMPOUNDS TO MUCOSAL SURFACES --.

<u>Column 14,</u>
Line 45, delete "malcate" and insert -- maleate --.

Signed and Sealed this

Twenty-third Day of April, 2002

*Attest:*

JAMES E. ROGAN
*Attesting Officer*     *Director of the United States Patent and Trademark Office*